(12) United States Patent
Popescu

(10) Patent No.: US 7,423,257 B2
(45) Date of Patent: Sep. 9, 2008

(54) SIGNAL TRANSMISSION DEVICE AND METHOD FOR TRANSFER OF SIGNALS BETWEEN TWO ELEMENTS MOVING RELATIVE TO ONE ANOTHER USING AN OPTICALLY-READABLE STRIP CONDUCTOR

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 477 days.

(21) Appl. No.: 11/250,859

(22) Filed: Oct. 14, 2005

(65) Prior Publication Data

US 2006/0099850 A1 May 11, 2006

(30) Foreign Application Priority Data

Oct. 15, 2004 (DE) .................. 10 2004 050 384

(51) Int. Cl.
*G01D 5/34* (2006.01)
(52) U.S. Cl. ................ 250/231.14; 250/227.14; 356/455
(58) Field of Classification Search ............ 250/231.14, 250/216, 227.14, 559.14; 356/455
See application file for complete search history.

(56) References Cited

U.S. PATENT DOCUMENTS

| | | | | |
|---|---|---|---|---|
| 4,201,474 A * | 5/1980 | Holl et al. | ............ | 356/369 |
| 5,140,696 A | 8/1992 | Fox | ............ | 455/41 |
| 5,535,033 A | 7/1996 | Guempelein et al. | ........ | 359/144 |
| 6,108,483 A * | 8/2000 | Berkcan | ............ | 385/147 |
| 6,301,324 B1 | 10/2001 | Pearson, Jr. et al. | ........ | 278/15 |
| 6,501,821 B2 | 12/2002 | Betz | ............ | 278/15 |
| 7,079,619 B2 * | 7/2006 | Katcha et al. | ........ | 378/15 |
| 7,102,472 B1 * | 9/2006 | Nathanson et al. | ........ | 335/78 |
| 2003/0214421 A1 | 11/2003 | Schilling | ........ | 340/370.37 |

(Continued)

FOREIGN PATENT DOCUMENTS

DE 41 37 032 A1 5/1993

(Continued)

OTHER PUBLICATIONS

"Liquid Crystals Line Up for VOAs," Freeman, Fibre Systems Europe, Dec. 2002, p. 9 and Oct. 2002, p. 11.

(Continued)

*Primary Examiner*—Georgia Y. Epps
*Assistant Examiner*—Kevin Wyatt
(74) *Attorney, Agent, or Firm*—Sdhiff Hardin LLP

(57) ABSTRACT

In a signal transmission device as well as a method for transmission of signals between two elements moving relative to one another, in particular for transfer of measurement and/or control data between a rotating part and a stationary part of a computed tomography apparatus, a transmission device with an RF strip conductor is used on a first of the two elements, the RF strip conductor is composed of a dielectric layer with electro-optical properties between two strips made of an electrically-conductive material, into which the signals are fed. In the method and the associated device, local temporal changes of optical properties of the dielectric layer that are electrically induced in the dielectric layer by the signals proceeding along the strip conductor are scanned with a light beam of a scanning unit arranged on the second element, at least during a movement segment of the relative movement of the two elements. The signal transmission device and associated method enable signal transmission with a high data rate.

17 Claims, 4 Drawing Sheets

U.S. PATENT DOCUMENTS

2005/0129345 A1 6/2005 Schilling ........................ 385/8

FOREIGN PATENT DOCUMENTS

DE  103 10 801 A1  10/2004

OTHER PUBLICATIONS

"Twice as Good," Matthews, Laser Focus World, Apr. 2003, pp. 62-67.

"VCSEL-Based Reflective Sensors Tackle More Demanding Applications," Tatum et al., Laser Focus World, Sep. 2003, pp. 79-83.

* cited by examiner

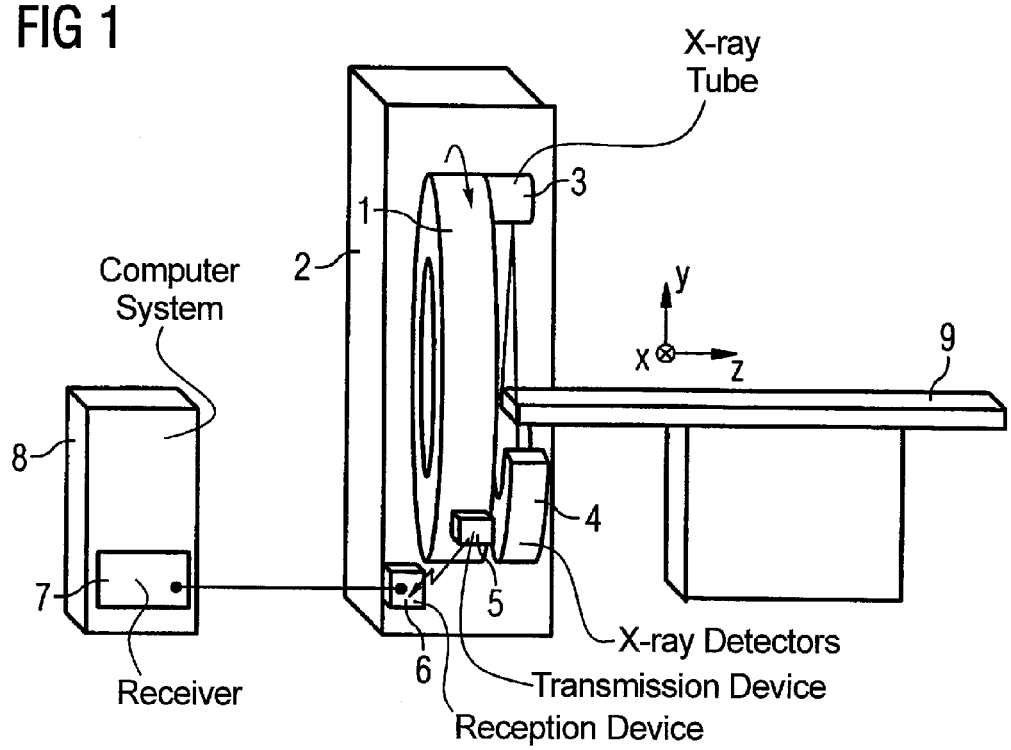
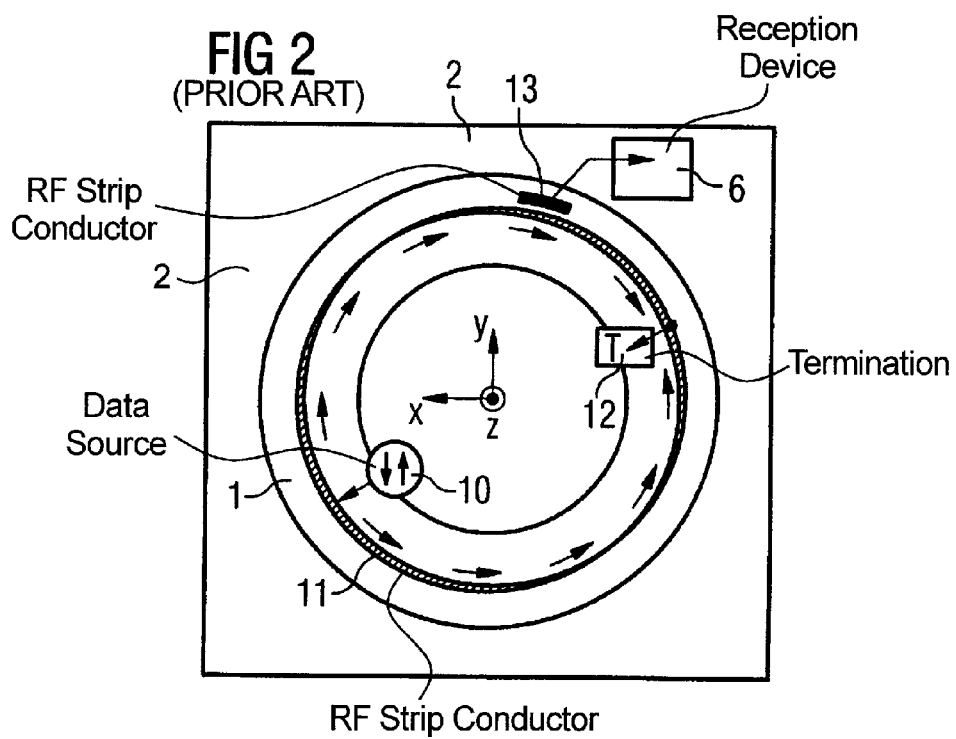

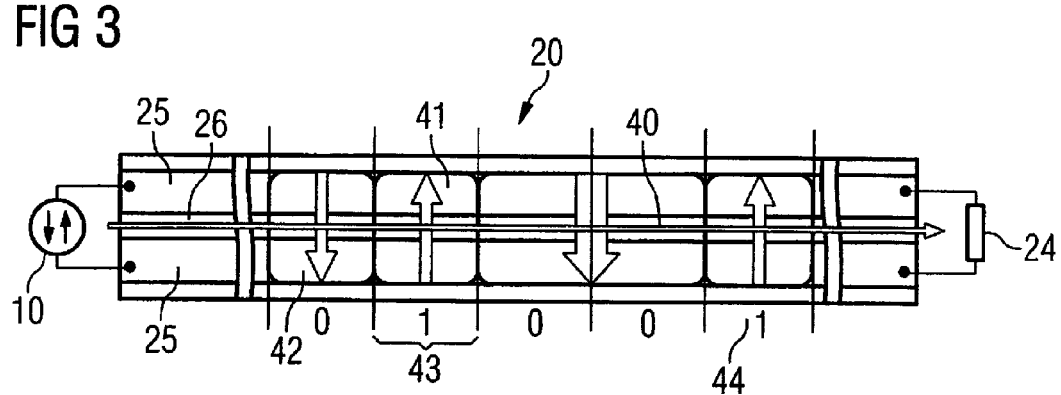
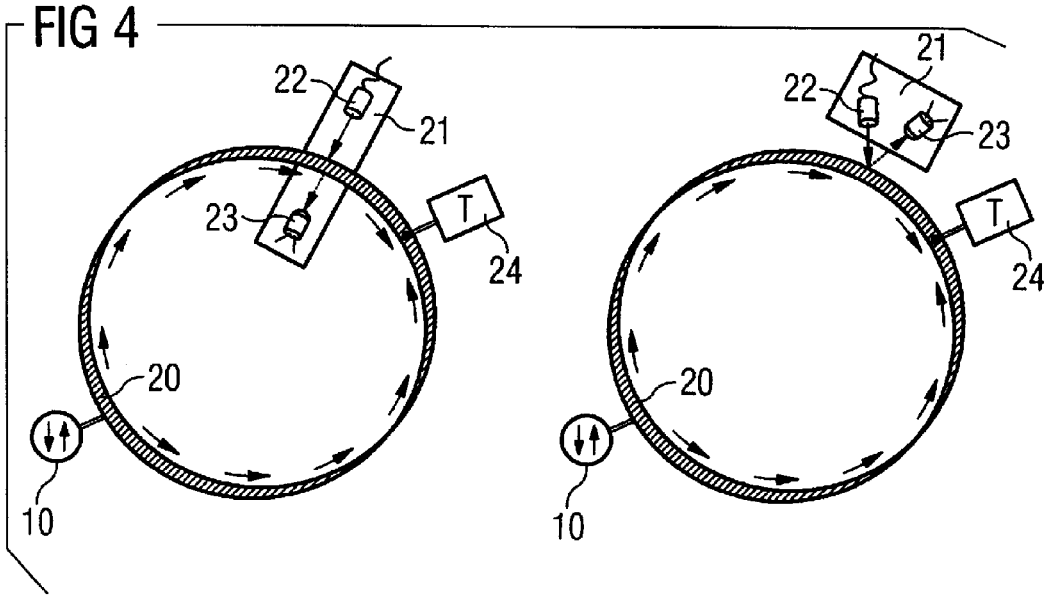

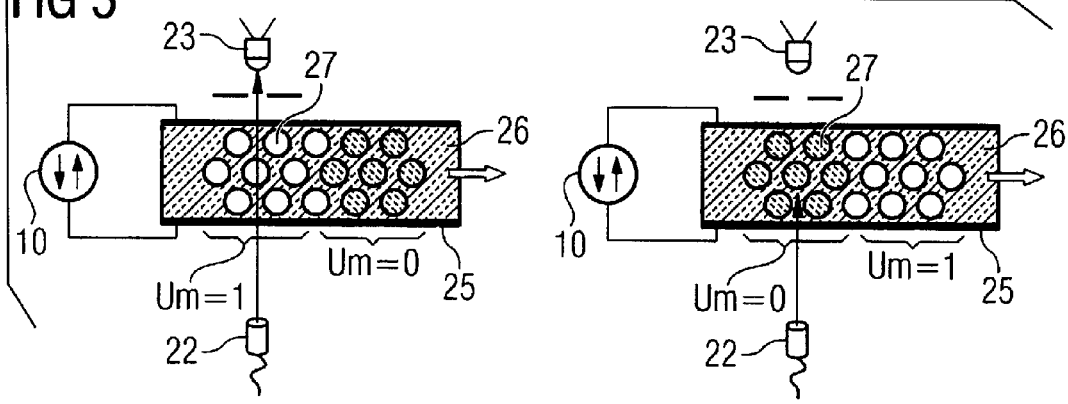
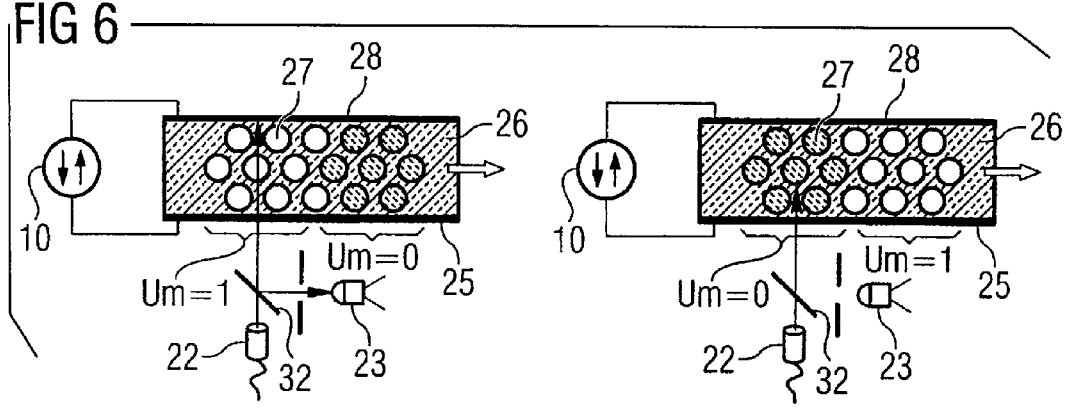
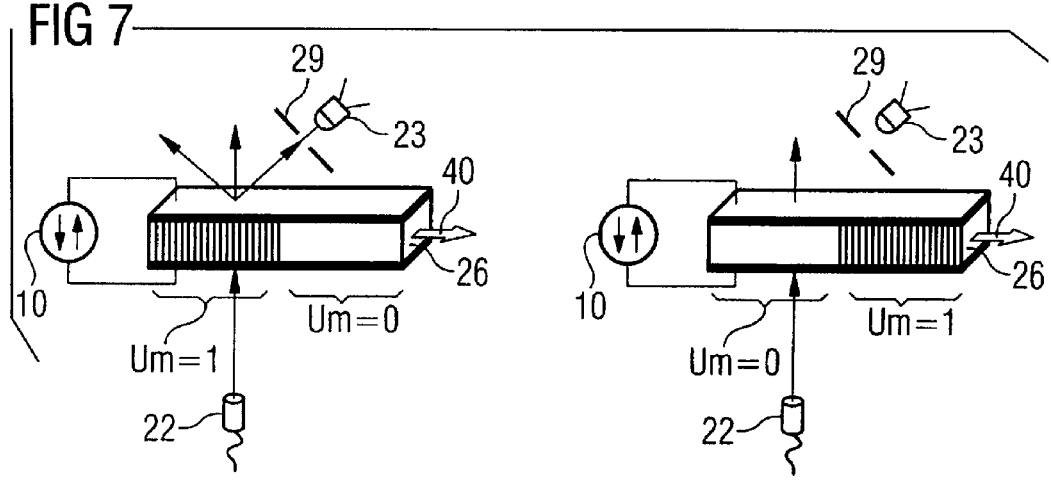

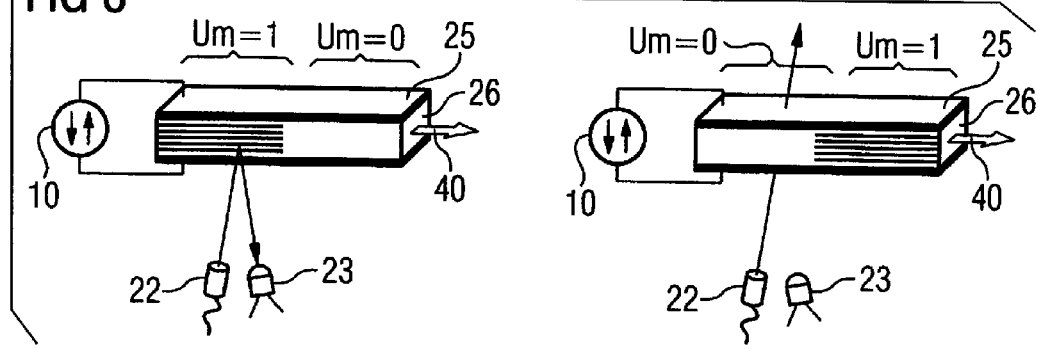
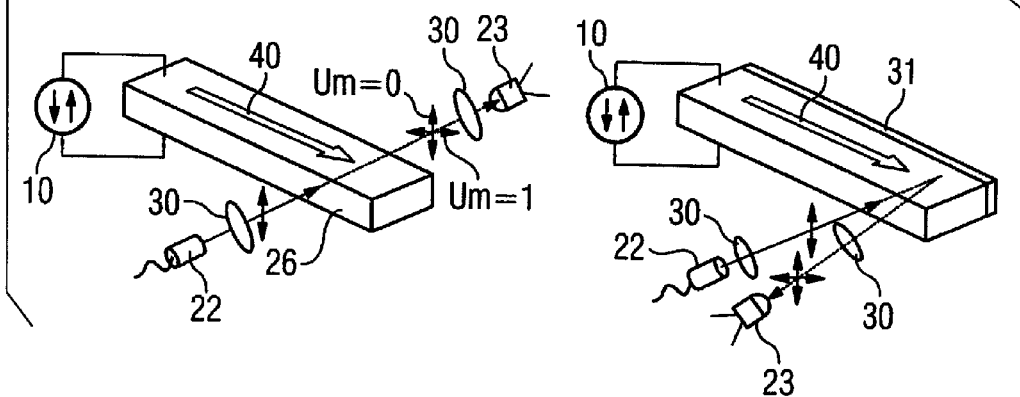

SIGNAL TRANSMISSION DEVICE AND METHOD FOR TRANSFER OF SIGNALS BETWEEN TWO ELEMENTS MOVING RELATIVE TO ONE ANOTHER USING AN OPTICALLY-READABLE STRIP CONDUCTOR

BACKGROUND OF THE INVENTION

1. Field of the Invention

The present invention concerns a signal transfer device for transmission of signals between two elements moving relative to one another, in particular for transfer of measurement and/or control data between a rotating part and a stationary part of a computed tomography apparatus, in which a transmission device with an RF strip conductor (stripline) on which the signals are conducted is attached on a first of the two elements and a reception device with a scanning unit is fastened on a second of the two elements, wherein the strip conductor and the scanning unit are arranged on the first and second elements such that the scanning unit moves along a longitudinal segment of the strip conductor at least during a movement segment of the relative movement of the two elements. The invention furthermore concerns a corresponding method for signal transfer.

2. Description of the Prior Art

In many technical fields large data quantities are to be transferred between elements moving relative to one another at a small distance, for example between individual apparatus parts of a measurement device. The data are normally acquired with a moving apparatus part and must be transferred to an evaluation device at a stationary apparatus part during the data acquisition. Medical imaging represents an example for such an application, and in particular computed tomography, in which a large quantity of measurement data must be transferred in real time during rotation from a rotating part of the gantry to the stationary part of the gantry. The available transfer rate represents an important criterion for the data quantity that can be transferred in real time.

Different technologies for the signal transmission between two elements moving relative to one another at a small distance are known that can be used in the field of computed tomography. In the previously most cost-effective and reliable solution, the transmission of the signals ensues via capacitive coupling from one transmitter mounted on a rotating part to an antenna arranged at a stationary part. DE 100 07 601 A1 describes a device for data transmission in which a waveguide is used as a transmitter. For the data transmission, the data are modulated on a carrier signal and injected into the waveguide. An antenna arranged in a geometrically-determined manner described in DE 100 07 601 A1 relative to the waveguide receives the carrier signal without contact so that the data are available at the stationary part after demodulation of the carrier signal. In the shown application, the waveguide is attached along the circumference of the C-arm of a C-arm x-ray apparatus and the antenna is attached on the supporting structure for this C-arm.

U.S. Pat. No. 5,140,696 describes a device for signal transmission between elements moving relative to one another, in particular in a computed tomography apparatus, in which a circular strip conductor is arranged on the circumference of the rotating part of the gantry as a transmitter and a short segment of a strip conductor is provided on the stationary part in the immediate proximity of the transmission line. The data transmission ensues in the same manner as in DE 100 07 601 A1. In these applications such strip conductors are frequently produced by a PCB technique (PCB: printed circuit board).

The continuously increasing (especially in the field of computed tomography) data quantity causes problems to be expected in the foreseeable future with this transfer technology. Modern multi-slice computed tomography system already generate data rates of many gigabits per second (Gbps). The physical bit length drops due to the increase in the data rate. The speed of the electromagnetic wave in a strip line is smaller than its speed in air, such that the bit length in the strip line is even shorter. While the receiving antenna in existing systems exhibits a length in the range of 6 to 22 cm, it must already be fashioned shorter than 2 cm given data transfer rates of 10 Gbps. This reduces the coupling capacity and therewith the signal-to-noise ratio, such that the transfer system reacts more sensitively to external interferences.

In addition to this capacitive transfer technology, individual solutions are also known for an optical transfer of the signals between the two elements moving relative to one another. For example, U.S. Pat. No. 5,535,033 discloses a signal transmission device in which a ring made of an optical waveguide is attached on the rotating part of a computed tomography gantry as a part of a transmission device that also radiates the injected light perpendicular to its longitudinal axis. The data to be transmitted are injected into this ring by modulation of the light source, and are received at the stationary part by an opto-electrical detector. Due to the annular design of the transmission device, reception of the data by the receiver is also possible during nearly every rotation phase. Optical data transfer technologies in which the signal is conducted in an optical fiber are, however, likewise limited in the achievable transfer rate due to self-phase modulation and group speed dispersion in the fiber.

SUMMARY OF THE INVENTION

An object of the present invention is to provide a device as well as a method for transfer of signals between two elements moving relative to one another, which enable data transfer with a data rate in the range of $\geq 10$ Gbps.

This object is achieved in accordance with the invention by a signal transmission device for transmission of signals between two elements moving relative to one another, in particular for transfer of measurement and/or control data between a rotating part and a stationary part of a computed tomography apparatus having, in a known manner, a transmission device with an RF strip conductor (on which the signals are conducted) on the first of the two elements and a reception device with a scanning unit on the second of the two elements. The strip conductor and the scanning unit are arranged on the first element and second elements such that the scanning unit moves along a longitudinal segment of the strip conductor at least during a movement segment of the relative movement of the two elements. In accordance with the invention the strip conductor is composed of a dielectric layer with electro-optical properties between two strips or layers made of an electrically-conductive material. In accordance with the invention, the scanning unit has at least one light source (preferably a laser) and an opto-electronic detector and is fashioned such that the light beam of the light source is directed on the dielectric layer of the strip conductor during the movement of the scanning unit along the longitudinal segment of the strip conductor, and a local temporal change of optical properties of the dielectric layer of the strip conductor, in particular of a micro-strip conductor, is detected by detection of reflected or transmitted or diffracted ray portions with the opto-electronic detector.

In conventional methods for such transfer of signals, the signals are fed into the strip conductor on the first element.

This ensues by suitable modulation of an RF carrier signal, as is also known regard to capacitive coupling. Since the dielectric layer of the strip conductor exhibits electro-optical properties, the optical properties of this layer are spatially and temporally modulated by the signals running across the strip conductor or by their electrical field. The local temporal changes of the optical properties induced by the signals in the dielectric layer are scanned with light (preferably a laser beam) of the scanning unit at least during a movement segment of the relative movement of the two elements, preferably during the entire movement. Depending on the induced optical changes, the light ray transmitted by the layer, reflected in the layer, or diffracted by the layer is used for the detection of the changes of the optical properties. The transmitted signals or data are re-acquired as an electrical signal or data sequence by translation of the detected changes by an opto-electronic detector.

In the inventive signal transmission device as well as in the associated method, the signals to be transmitted are injected into a strip conductor in the same manner as in the capacitive technique explained above. In accordance with the invention, however, a strip conductor with a particular material of the dielectric layer that exhibits electro-optical properties is used. Furthermore, in contrast to the known technique of the capacitive coupling, the signals proceeding along the strip conductor are not received with an antenna, but are scanned or read out with a light ray that is directed on the dielectric layer of the strip conductor. Changes of the optical properties in the dielectric layer that are induced in the layer due to the electro-optical properties of the layer by the electrical fields (modulated in terms of amplitude) of the signals proceeding along the strip conductor are made visible by the light ray. The readout of these changes ensues in connection with at least one opto-electronic detector on which transmitted, reflected or diffracted ray portions of the light ray impact. The bit pattern proceeding along the strip conductor can be read out without contact in this manner.

Individual embodiments of the invention with a laser as the light source are explained below. Depending on the requirements for the beam properties and the transfer rate, other light sources (for example light-emitting diodes) naturally can be used.

Since different electro-optical effects can be used in the method, different arrangements of the light source and detector can be used that are explained in detail below. This also concerns the beam path of the light source transverse to the longitudinal extension of the strip conductor. Depending on the utilized electro-optical effect that results from the selection of the material and of the design of the dielectric layer, this beam path can proceed through one or both strips made of the electrically-conductive material, or between these strips. In one embodiment, at least one of the strips is formed of electrically-conductive material that is transparent for the light beam such as, for example, a transparent, electrically-conductive oxide (TCO). Such transparent, electrically-conductive oxides are, for example, the oxides of tin, indium, cadmium, gallium, copper or zinc as are known from the field of liquid crystal displays, solar cells and thermally-insulating glazes for window surfaces. Preferably, both electrically-conductive strips of the strip conductor are composed of such a material.

Given the proposed signal transmission device and the associated method, the material of the dielectric layer of the strip conductor is naturally selected with regard to its electro-optical properties such that the changes of the optical properties that are induced by the injected signals in the layer can be detected with the scanning device, i.e. the light source and the optical detector. For example, liquid crystals dispersed in a polymer or polymers or ferro-electric materials with non-linear optical effects can thereby be used as electro-optical materials. Examples for the last-cited materials are ADP ($NH_4H_2PO_4$), KDP ($KH_2PO_4$), $LiNbO_3$, $LiTaO_3$ or CdTe. A design of the dielectric layer from different sub-layers of electro-optical materials in order to generate an electrically-induced Bragg lattice can also be used according to a further embodiment of the invention, as well in the associated method.

In principle, the inventive signal transmission device can be used for different movement patterns of the elements that move relative to one another. Given a straight-line movement, the strip conductor can proceed in a straight line on the stationary or moving part such that it is directed sufficiently close to the scanning device over an optimally large segment of the movement. Given a rotation movement of the moving element, the strip conductor preferably proceeds, at least in segments, on an orbit (circular path) around the rotation center. Naturally it is possible for both elements to move in the relative movement. Signal transmission is possible only in the segment of the relative movement in which the light or laser beam of the scanning device strikes the dielectric layer of the strip conductor. The data transfer is interrupted in the remaining segments of the movement. An interruption-free data transfer can be achieved, for example, by having the strip conductor extend across the entire route segment of the relative movement, or by arranging a number of strip conductors suitably offset relative to one another in order to allow scanning by the laser beam at every point in time of the movement, in which case a number of scanning units can also be provided. The one or more strip conductors of the present transmission device are terminated with an impedance at their end opposite the coupling-in point of the signals in order to prevent reflections of the signals at this end.

The present signal transmission device as well as the associated method enable a substantially continuous signal or measurement data transmission with a transfer rate that is superior to the known solutions. Given use in a computed tomography apparatus, the strip conductor is preferably attached on the rotating part of the gantry in order to enable a transfer of the measurement data to the stationary part of the gantry. A transmission device with at least one strip conductor naturally can also be arranged on the stationary part in order to enable a transfer of control data to the rotating part, which then carries a corresponding scanning device. The entire scanning device can be fashioned with a large savings of weight and space by the use of a semiconductor laser.

Furthermore, the present signal transmission device enables the use of a number of strip conductors lying next to one another for the parallel transfer of signals. These strip conductors running next to one another are then simultaneously scanned with different laser beams with the scanning device. The width of the strip conductors in the present signal transmission device as well as in the associated method can lie below one centimeter, for example in the range of only 1 mm, since such narrow strip conductors can also be scanned without anything further with a focused laser beam. A number of strip conductors with sufficient separation (to prevent crosstalk) can be arranged next to one another in order to correspondingly increase the transferable data rate. Even when the data bits propagating on a strip conductor exhibit lengths of less than 1 cm due to the high data rates, these bit signals can likewise be scanned without anything further with a focused laser beam. The requirements for the retention of a sufficiently small separation between the strip conductor and the scanning device are distinctly less than in the known technology of the capacitive coupling. The present signal transmission device is distinctly less sensitive to mechanical tolerances. The components of the transmission and reception device are galvanically isolated and completely potential-free. The present method as well as the associated device are therefore insensitive relative to common mode interferences between the rotating and the stationary part of a computed tomography apparatus and likewise relative to external electrical interferences.

DESCRIPTION OF THET DRAWINGS

FIG. 1 is a schematic representation of a computed tomography apparatus with the associated signal transmission system.

FIG. 2 shows an example for a signal transmission device of a computed tomography apparatus according to the prior art in schematic representation.

FIG. 3 shows an example for the design of the RF strip conductor of the transmission device according to the present invention.

FIG. 4 shows two examples for the arrangement of laser and opto-electronic detector and of the scanning unit according to the present invention.

FIG. 5 shows an example for the scanning of the strip conductor according to the present invention.

FIG. 6 shows a further example for the scanning of the strip conductor according to the present invention.

FIG. 7 shows a further example for the scanning of the strip conductor according to the present invention.

FIG. 8 shows a further example for the scanning of the strip conductor according to the present invention.

FIG. 9 shows two further examples for the scanning of the strip conductor according to the present invention.

DESCRIPTION OF THE PREFERRED EMBODIMENTS

In schematic representation, FIG. 1 shows a computed tomography apparatus with a signal transmission device for transfer of measurement data from the rotating part to the stationary part of the gantry. Among other things, the computed tomography apparatus has an x-ray tube 3, x-ray detectors 4 arranged in rows, and a patient support table 9. The x-ray tube 3 and the x-ray detectors 4 are arranged on the rotating part 1 of a gantry that rotates around the patient support table 9, or an examination axis running parallel thereto. The patient support table 9 normally can be shifted relative the gantry along the examination axis. The x-ray tube 3 generates an x-ray beam expanding in a fan shape in a slice plane perpendicular to the examination axis, which x-ray beam penetrates a slice of a subject (for example a body slice of a patient who is positioned on the patient support table 9) in examinations in the slice plane, and the x-ray beam striking on the x-ray detectors 4 opposite the x-ray tube after being attenuated by the patient 3. The angle at which the x-ray beam penetrates the body slice of the patient, and possibly the position of the patient support table 9 relative to the gantry, vary continuously during the image data acquisition with the computed tomography apparatus. During the image data acquisition, the x-ray detectors 4 therefore deliver a large quantity of measurement data that must be evaluated for reconstruction of a two-dimensional slice image or a three-dimensional image of the body of the patient. This evaluation normally ensues in a stationary computer system 8 that is connected with the computed tomography apparatus. During the measurement data acquisition, the rotating part 1 of the gantry rotates inside the stationary part 2. The measurement data acquired by the x-ray detectors 4 are transferred to a stationary reception device 6 on the stationary part 2 of the computed tomography apparatus with a rotating transmission device 5 that is attached on the rotating part 1 of the gantry. The data are then normally supplied from the stationary reception device 6 to a receiver 7 of the image computer 8 via a cable connection for evaluation.

FIG. 2 shows an embodiment of a known transmission device of the prior art in a schematized representation, as used in numerous computed tomography apparatus. In this data transmission device, the measurement data are transferred from the rotating part 1 of the gantry to the stationary part 2 of the gantry via capacitive coupling. For this, a circular RF strip conductor 11 is attached on the rotating part 1 as a transmission antenna into which the measurement data are injected from the data source 10. The strip conductor 11 is terminated by a suitable impedance on the side opposite the feed point. The data bits fed by the data source 10 into the strip conductor 11 propagate in both branches of the strip conductor 11 up to the termination 12. The division into two branches extending in opposite directions enables a continuous data transmission during the rotation of the gantry. The arrows in FIG. 2 show the propagation direction of the data signals in both branches of the strip conductor 11. On the stationary part 2 of the gantry, a shorter segment of an RF strip conductor 13 is arranged as a reception antenna that is part of the reception device 6 of the stationary part 2. Given the rotation of the rotating part 1 of the gantry, the reception antenna (strip conductor 13) is located in the immediate proximity of the strip conductor 11 (used as a transmission antenna) of the rotating part 1, such that the data signals injected into the strip conductor 11 are received by the reception antenna via capacitive coupling. This type of data transmission encounters problems at higher data rates and the shortening of the reception antenna thereby required, as explained in above.

In the signal transmission device according to the present invention, an RF strip conductor (in particular a micro-strip conductor) is likewise used as a part of the transmission device. Given use in a computed tomography apparatus, this strip conductor can be arranged in the rotating part 1 of the gantry in the same manner as this is shown in FIG. 2. The strip conductor, into which the data signals are injected into the same manner as in the known systems with capacitive coupling, is likewise suitably terminated at its end opposite the coupling point in order to prevent reflections of the signals at these ends.

FIG. 3 shows an example for the design of the RF strip conductor used in the present invention. The signals, which exist in the form of individual data bits 44, are injected by the data source 10 into the strip conductor 20 and propagate in the strip conductor 20 up to the opposite end and the termination 24 provided there. The propagation direction 40 of the data bits 44 or of the modulated electrical field forming these is illustrated with the long extended arrow of FIG. 3. The strip conductor 20 is comprised of two thin strips 25 of an electrically-conductive material, for example copper, between which is arranged a dielectric layer 26 made from a material with electro-optical properties. In FIG. 3, the effect of the data bits 44 propagating on the strip conductor 20 is illustrated by its electrical fields 41, 42 on the dielectric 26. Coding of the data bits is hereby exemplarily assumed in which the electrical field 41 for a data bit with the logic value "1" is directed in the direction opposite that of the electrical field 42 of a data bit with the logic value "0". The length of a propagating data bit 44 in the strip conductor is indicated with the reference character 43. From FIG. 3 it can be seen that the electromagnetic field modulated with the data bits 44, which electromagnetic field propagates in the strip conductor, influences the optical properties of the dielectric layer (that essentially follow the data pattern) given a dielectric layer 26 made of a material with electro-optical properties.

This physical effect is utilized in the inventive signal transmission device as well as in the associated method in order to optically read out the signals (data bits) 44 propagating on the strip conductor. A reception device with a scanning unit 21 is used on the stationary part 2, the scanning unit 21 having at least one laser 22 as well as a photodetector 23 as can be seen from FIG. 4. The readout of the data bits by detecting the local temporal change of the optical properties of the dielectric layer 26 of the strip conductor 20 can ensue in the arrangement as shown in the left part of FIG. 4. The laser beam of the laser 22 transirradiates the dielectric layer of the rotation strip conductor 20, and the photodetector 23 is located on the side of the strip conductor 20 opposite the laser 22. In a different shown in the right part of FIG. 4, both the laser 22 and the photodetector 23 are on the same side of the strip conductor 20, with the laser beam that penetrates into the dielectric layer being reflected behind the layer (in terms of the beam direction), and penetrating the dielectric layer again and then striking on the photodetector 23. This reflection can be achieved by a mirrored surface behind the strip conductor or by the use of a reflecting, electrically-conductive material for the back side strips of the strip conductor. A semiconductor laser can be used as a laser in this and all other embodiments, preferably a VCSEL (Vertical Cavity Surface Emitting Laser).

The following embodiments exemplify different arrangement possibilities for the laser as well as the photodetector within the scanning unit 21, dependent on different electro-optical materials and a different design of the dielectric layer 26 of the strip conductor 20. In these exemplary embodiments, coding of the data bits ensues as an example wherein a data bit with the logic value "1" is represented in the data stream by a time segment with an electrical field of a specific magnitude (Um=1) and a data bit with the logical value "0" is represented in the data stream by a time segment without an electrical field (Um=0).

A material for the dielectric layer 26 is used in FIG. 5 that is composed of a polymer matrix in which the liquid crystals 27 are dispersed. Both electrically-conductive strips 25 between which the dielectric layer 26 is fashioned are, in this example, composed of an optically-transparent material. FIG. 5 shows a scanning unit in which the laser 22 and the photodetector 23 are on opposite sides of the strip conductor 20 and the laser beam penetrates the strip conductor 20 perpendicular to its longitudinal extension and to the electrically-conductive strips 25. If an electrical field is now applied between the two strips 25 at the point at which the laser beam penetrates the dielectric layer 26, the liquid crystals align at this point such that the layer is transparent for the laser beam (Um=1; left image). If no electrical field is applied at this point (Um=1; right image), the material is not transparent for the laser beam. In the coding of the data bits explained above, the transmission of the dielectric layer for the laser beam is thus temporally changed by the data bits propagating in the strip conductor. The electro-optical properties of this dielectric material thus form the data bits transmitted by the strip conductor to the optical transmission of the material. The modulation of the transmission of the laser beam detected by the photodetector 23 thus corresponds to the data pattern transmitted via the strip conductor.

Given use of such an electro-optical material as a dielectric material 26 in which the transmission changes with the applied electrical field, a different arrangement of laser 22 and photodetector 23 can also be selected in the scanning unit as illustrated in FIG. 6. Here the laser beam is reflected back on the back-side (viewed in the beam propagation direction), electrically-conductive strip that is fashioned as a mirror 28 for the laser radiation, such that it passes through the dielectric layer 26 twice. The beam portion passing back can be directed onto the photodetector 23 via a semi-permeable mirror 32 in the beam path of the laser beam. The optical transmission of the dielectric layer 26 that is modulated by the propagating data bits is also detected by this arrangement.

FIG. 7 shows a further possibility of an embodiment of the strip conductor 20 of the inventive signal transmission device in which the diffraction of the laser beam via an electro-optical Bragg grating induced in the dielectric layer 26 is used. The dielectric layer 26 is thereby made up of a plurality of transversal sub-layers (i.e. sub-layers running perpendicular to the strips 25) of a non-linear electro-optical material, whereby successive sub-layers respectively exhibit reversed crystal orientation and the thickness of the sub-layers is adapted to the coherence length of the laser radiation (phase adaptation). For example, lithium niobate ($LiNbO_3$) or other ferro-electric materials suitable for this application can be used as materials for the sub-layers. No Bragg grating arises in the absence of an electrical field across the dielectric layer, but an electrical field of a data bit with the logic value "1" generates a Bragg grating at this point (Um=1), as is illustrated in FIG. 7. The laser beam striking at this point on the layer is then diffracted with different diffraction orders. If the photodetector 23 is arranged at a point at which the first or a higher diffraction order arises, laser intensity is only measured when an electrical field is directly applied at this point. If no electrical field is applied (Um=0; compare right part of FIG. 7), the laser beam is not diffracted such that no beam portion reaches on the photodetector 23.

In the example of FIG. 7, use is made of the fact that the electrical field applied between the optically-conductive strips 25 of the strip conductor and propagating along the strip conductor changes the local refraction index of the transversal sub-layers corresponding to the transferred bit pattern. In this example, the electrically-conductive strips 25 are also formed of transparent oxides. A data bit with the logic value "1" generates an electrical field via which a temporary lattice structure is formed in the dielectric layer 26 that generates a plurality of diffraction orders according to the Laue equation: $\sin \theta_m = m^* \lambda/d$, whereby $\theta$ corresponds to the angle of diffraction, $\lambda$ corresponds to the coherent wavelength of the laser and d corresponds to the lattice constant, and m=0, 1, . . . $\leq d/\lambda$. An additional collimator 19 (for example in the form of a diaphragm) via which interferences with random light reflections are prevented can be used to improve the directional sensitivity of the used photodetector 23. A data bit with the logic value "0" generates no electrical field across the dielectric layer 26 and thus does not alter the properties of the slice material. Given a homogenous optical material, in this case the laser beam passes through the dielectric layer 26 without diffraction.

The change of the refraction index by the modulated data bit stream can be very small. A diffraction index change of 0.0001 is sufficient in order to generate an effective Bragg grating since a very large number of periods lie within the length of one data bit, or the length of the grating thereby induced. Thus, for example, given a transfer rate of 20 Gbps, a 1 cm-long grating encompasses more than 10,000 wavelength periods for laser radiation with a wavelength of 660 nm, and thus can be used for the readout of the dielectric layer.

Given this embodiment of the dielectric layer, the scanning unit can naturally also be operated in a back-reflection arrangement, with the laser and the photodetector then arranged on the same side. The photodetector hereby merely has to be positioned at the point of the respective diffraction order that is to be detected for the light being deflected back.

FIG. 8 shows a further example for the design of the dielectric material of the strip conductor 20 in which a Bragg grating is likewise induced in the dielectric layer. In this example, the dielectric layer 26 is designed so that the individual sub-layers run longitudinally, i.e. parallel to the strips 25. The layer thickness is in turn adapted to the coherence length of the radiated laser light (phase adaptation). Otherwise, the same considerations apply as in connection with FIG. 7. FIG. 8 shows an arrangement of the laser as well as of the photodetector in which a measurement of return reflection ensues. An arrangement of the laser and photodetector also naturally can be selected as it is shown in FIG. 7.

FIG. 9 shows two further examples for the formation of the strip conductor and the scanning unit. In these examples, the material of the dielectric layer 26 is selected so that the Pockel effect occurs upon application of an electrical field. The polarization direction of the polarized laser beam passing through the layer is thus changed by the electrical field of the transmitted data bits. This temporal change (modulated by the data bits) of the polarization can be detected by the photodetector 23 by suitably adjusted linear polarizers 30.

In the embodiment according to the left illustration of FIG. 9, a defined linear polarization of the laser beam is initially adjusted with the linear polarizer 30. The linearly-polarized laser beam penetrates the dielectric layer 26 between the electrically-conductive strips 25, with the polarization changing dependent on the application or non-application of an electrical field between the electrically-conductive strips 25. For a logic bit value of "1", the polarization plane rotates by 90° such that no laser light arrives at the detector 23 given arrangement of a second linear polarizer 30 in front of the photodetector 23. The detector thus outputs the logic value "0". A data bit with the logic value "0" does not change the polarization plane of the radiated laser light, such that the light reaches the detector 23 and thus generates a logic value of "1".

In the embodiment according to the right part of FIG. 9, in which the return reflection on a mirror 31 is used for the double passage of the laser beam through the dielectric layer 26, the electrical field strength necessary for the generation of the Pockel effect is lower. In both shown embodiments, an arrangement of a transversal Pockel modulator is used in which the electrodes or, respectively, electrically-conductive strips 25 do not interfere with the laser beam. The phase shift is proportional to the product of the electrical field and the length of the optical path through the dielectric layer. The modulation voltage therefore can be reduced to a few volts, by lengthening the optical path length.

In a development, this correlation is utilized in order to compensate for an attenuation of the electrical field of the data bits over the length of the strip conductor with regard to the generated phase shift. For this purpose, the width of the dielectric layer is made to increase with the distance from the coupling point of the data bits in the strip conductor, in order to obtain a constant phase shift at every point of the strip conductor via the Pockel effect.

As an alternative to this transversal configuration, the strip conductor can also be designed as a longitudinal Pockel modulator. Longitudinal modulators exhibit a degree of the phase shift (Pockel effect) that is independent of the thickness of the dielectric layer or of the optical path length through the dielectric layer. The phase shift is merely proportional to the modulation voltage that, in this case, must be greater than in the transversal configuration. Furthermore, in such an embodiment the electrically-conductive strips must be optically transparent for the laser radiation. In this case, the strip conductor can be composed, for example, of a crystal forming the dielectric layer, the surface of which is coated on both sides with a layer of tin oxide. The longitudinal arrangement has the advantage of a higher discharge ratio relative to a transversal modulator.

Although modifications and changes may be suggested by those skilled in the art, it is the intention of the inventors to embody within the patent warranted hereon all changes and modifications as reasonably and properly come within the scope of their contribution to the art.

I claim:

1. A signal transmission device for transmitting a signal between two elements that are moving relative to each other, comprising:

a signal transmission device comprising at least one RF strip conductor, mounted on a first of said two elements;

a reception device comprising at least one scanning unit for said RF strip conductor mounted at a second of said two elements;

said strip conductor and said scanning unit being mounted respectively on said first of said elements and said of second of said elements to cause said scanning unit to move along a longitudinal section of said strip conductor during at least a portion of the relative movement of the two elements;

said strip conductor comprising a dielectric layer having electro-optical properties disposed between two electrically conductive strips, across which said signal is fed, said electro-optical properties locally and temporally changing dependent on said signal; and said scanning unit comprising a light source and an opto-electronic detector, said light source emitting a light beam that interacts with said dielectric layer as said scanning unit moves with said second of said elements along said longitudinal section of said strip conductor, said localized, temporal changes in said electro-optical properties of said dielectric layer altering said light beam, and said altered light beam being detected by said opto-electronic detector.

2. A signal transmission device as claimed in claim 1 wherein at least one of said strips of said strip conductor is comprised of electrically-conductive material that is optically transparent to said light emitted by said light source.

3. A signal transmission device as claimed in claim 2 wherein said scanning unit is disposed relative to said strip conductor so that said light penetrates through said strip conductor transversely to said longitudinal section to strike said detector.

4. A signal transmission device as claimed in claim 2 wherein said strip conductor comprises a reflecting surface disposed behind said dielectric layer, and wherein said scanning unit is disposed relative to said strip conductor so that said light penetrates said dielectric layer transversely to said longitudinal section, is reflected by said reflector and again penetrates said dielectric layer transversely to said longitudinal section and strikes said detector.

5. A signal transmission device as claimed in claim 2 wherein said dielectric layer forms an electrically induced Bragg grating in the presence of an electrical field caused by said signal, and wherein said scanning unit is disposed relative to said strip conductor so that only portions of said light diffracted by said Bragg grating, and having a diffraction order higher than zero, strike said detector.

6. A signal transmission device as claimed in claim 1 wherein said strip conductor causes a rotation of a polarization plane of said light from said light source dependent on said signal, and wherein said scanning unit comprises a polarizer allowing only light having said rotation in said polarization plane to strike said detector.

7. A signal transmission device as claimed in claim 1 wherein said dielectric layer comprises liquid crystals dispersed in a polymer matrix, and wherein at least one of said strips of said strip conductor is comprised of an electrically-conductive material transparent to said light from said light source.

8. A signal transmission device as claimed in claim 1 wherein said dielectric layer is comprised of a material having non-linear optical properties.

9. A signal transmission device as claimed in claim 1 wherein one of said strips of said strip conductor, disposed between said dielectric layer and said light source, is comprised of electrically-conductive material that is transparent to said light emitted by said light source, and wherein said dielectric layer forms an electrically-induced Bragg grating dependent on an electrical field generated by said signal, and wherein said scanning unit allows only light diffracted by said Bragg grating and having a diffraction order higher than zero to strike said detector, and wherein said dielectric layer is comprised of a plurality of sub-layers forming said electrically-induced Bragg grating.

10. A signal transmission device as claimed in claim 1 wherein one of said two elements rotates around a rotation axis and is disposed in a plane perpendicular to said rotation axis, and wherein said strip conductor occupies at least a portion of an orbit around said rotation axis.

11. A signal transmission device as claimed in claim 1 wherein said transmission device comprises a transmission modulator that modulates said signal and wherein said reception device comprises a reception demodulator that demodulates the modulated signal.

12. A signal transmission device as claimed in claim 1 wherein said transmission device is adapted to be disposed on a rotating part of a computed tomography apparatus, as said first of said elements, and wherein said reception device is adapted to be mounted on a stationary part of said computer tomography apparatus, as said second of said elements.

13. A signal transmission device as claimed in claim 1 wherein said light source is a laser.

14. A method for transmitting a signal between two elements moving relative to each other, a first of said elements having an RF strip conductor mounted thereon and a second of said elements having a scanning unit mounted thereon, said RF strip conductor comprising a dielectric layer having electro-optical properties disposed between two strips comprised of electrically conductive material and said scanning unit comprising a light source that emits light and an opto-electronic detector, said method comprising the steps of:

feeding said signal into said RF strip conductor and thereby altering said electro-optical properties of said dielectric layer;

irradiating said RF strip conductor with said light from said light source during said movement of said elements relative to each other, said changes in said electro-optical properties of said dielectric layer altering said light beam; and detecting the altered light beam with said opto-electronic detector.

15. A method as claimed in claim 14 comprising forming said dielectric layer of a material in which said signal induces a temporary change in optical transmission of said light through said dielectric layer.

16. A method as claimed in claim 14 comprising forming said dielectric layer of a material in which said signal induces a temporary change in optical polarization of said light through said dielectric layer.

17. A method as claimed in claim 14 comprising forming said dielectric layer of material in which said signal induces a change of a degree of diffraction of said light in said dielectric layer.

* * * * *